United States Patent
Jakkula (10) Patent No.: US 10,302,576 B2
(45) Date of Patent: May 28, 2019

(54) APPARATUS AND METHOD FOR MEASURING FLOWABLE SUBSTANCE AND ARRANGEMENT AND METHOD FOR CONTROLLING SOLID CONTENT OF FLOWABLE SUBSTANCE

(71) Applicant: SENFIT OY, Oulu (FI)

(72) Inventor: Pekka Jakkula, Oulu (FI)

(73) Assignee: SENFIT OY, Oulu (FI)

( * ) Notice: Subject to any disclaimer, the term of this patent is extended or adjusted under 35 U.S.C. 154(b) by 0 days.

(21) Appl. No.: 15/524,938

(22) PCT Filed: Nov. 10, 2015

(86) PCT No.: PCT/FI2015/050777
§ 371 (c)(1),
(2) Date: May 5, 2017

(87) PCT Pub. No.: WO2016/075367
PCT Pub. Date: May 19, 2016

(65) Prior Publication Data
US 2017/0343484 A1    Nov. 30, 2017

(30) Foreign Application Priority Data
Nov. 10, 2014   (FI) ...................................... 20145983

(51) Int. Cl.
*G01N 22/00*      (2006.01)
*C02F 1/52*       (2006.01)
*B01D 21/34*      (2006.01)

(52) U.S. Cl.
CPC ............ *G01N 22/00* (2013.01); *B01D 21/34* (2013.01); *C02F 1/52* (2013.01)

(58) Field of Classification Search
CPC ............ G01N 22/00; C02F 1/52; B01D 21/34
(Continued)

(56) References Cited

U.S. PATENT DOCUMENTS 4,888,547 A * 12/1989 McGinn .................. G01F 1/712
                                                         73/861
5,103,181 A *  4/1992 Gaisford ............ G01N 33/2823
                                                         324/637
(Continued)

FOREIGN PATENT DOCUMENTS

DE    10210511 B4 * 11/2005 ............ B01F 3/1221
EP    0926487 A1    6/1999
(Continued)

OTHER PUBLICATIONS

Dec. 23, 2015 Search Report issued in International Application No. PCT/FI2015/050777.
(Continued)

*Primary Examiner* — Patrick Assouad
*Assistant Examiner* — Sean Curtis
(74) *Attorney, Agent, or Firm* — Oliff PLC (57) ABSTRACT

An apparatus for measuring flowable substance which has at least three microwave sensor elements arranged at separate locations in a measurement chamber in contact with the flowable substance. The sensor elements operate as at least two transmitter-receiver pairs, which transmit and receive microwave radiation via at last two paths of different lengths, through layers of dirt on the sensor elements and the flowable substance for eliminating an effect of dirt layers on the sensor elements from the measurement result. A signal processing unit has a controller which is configured to control feed of at least one substance which has an effect on the measured value of the flowable substance to the chamber on the basis of the measured value of the desired property of the flowable substance.

11 Claims, 6 Drawing Sheets

(58) Field of Classification Search
USPC .............. 324/629, 250, 306, 637; 73/861.11
See application file for complete search history.

(56) References Cited

U.S. PATENT DOCUMENTS

| | | | | |
|---|---|---|---|---|
| 5,386,719 A * | 2/1995 | Marrelli | ................. | G01N 22/00 324/640 |
| 5,502,393 A * | 3/1996 | Yamaguchi | ............ | G01N 22/00 324/637 |
| 5,581,191 A * | 12/1996 | Yamaguchi | .............. | G01N 9/24 324/637 |
| 5,610,527 A * | 3/1997 | Yamaguchi | ............ | G01N 22/00 324/639 |
| 5,767,409 A * | 6/1998 | Yamaguchi | ............ | G01N 22/00 250/301 |
| 5,969,254 A * | 10/1999 | Yamaguchi | ............ | G01N 22/00 250/301 |
| 6,260,406 B1 * | 7/2001 | Shimokawa | ............. | G01N 9/24 73/32 R |
| 6,268,736 B1 * | 7/2001 | Hirai | ...................... | G01N 22/00 324/637 |
| 6,794,865 B2 * | 9/2004 | Astley | .................. | G01R 33/563 324/306 |
| 7,164,123 B2 * | 1/2007 | Morris | ................... | G01N 24/08 250/287 |
| 7,589,529 B1 * | 9/2009 | White | ................... | G01N 24/08 324/306 |
| 7,648,836 B1 * | 1/2010 | Scott | ...................... | G01N 22/00 422/416 |
| 7,683,613 B2 * | 3/2010 | Freedman | ............ | G01N 24/081 324/303 |
| 7,927,875 B1 * | 4/2011 | Scott | ...................... | G01N 22/00 436/39 |
| 9,970,804 B2 * | 5/2018 | Abou Khousa | ......... | G01F 1/708 |
| 2004/0229376 A1 * | 11/2004 | Beauducel | .......... | G01F 23/2845 436/164 |
| 2006/0052963 A1 * | 3/2006 | Shkarlet | .................. | G01F 1/668 702/108 |
| 2006/0164085 A1 * | 7/2006 | Morris | ................... | G01N 24/08 324/307 |
| 2007/0279073 A1 * | 12/2007 | Wee | .................... | G01N 33/2823 324/639 |
| 2011/0267074 A1 * | 11/2011 | Xie | ........................ | G01N 22/00 324/629 |
| 2012/0143529 A1 * | 6/2012 | Dam | .................... | G01N 29/024 702/48 |
| 2012/0265454 A1 * | 10/2012 | Rudd | ...................... | G01F 1/667 702/48 |
| 2015/0300936 A1 * | 10/2015 | Edward | ............. | G01N 33/2847 324/629 |
| 2015/0355110 A1 * | 12/2015 | Sappok | ................... | G01N 1/44 324/639 |
| 2016/0054161 A1 * | 2/2016 | Abou Khousa | ......... | G01F 1/708 73/861.04 |

FOREIGN PATENT DOCUMENTS

| | | |
|---|---|---|
| JP | 2001-255284 A | 9/2001 |
| JP | 2002-350364 A | 12/2002 |
| WO | 9105243 A1 | 4/1991 |
| WO | 98/53306 A1 | 11/1998 |

OTHER PUBLICATIONS

Jul. 6, 2015 Search Report issued in Finnish Patent Application No. 20145983.

Dec. 23, 2015 Written Opinion issued in International Application No. PCT/FI2015/050777.

Sep. 5, 2017 Extended European Search Report issued in European Patent Application No. 15859228.7.

Saber, Nasser et al. "A Feasibility Study on the Application of Microwaves for Online Biofilm Monitoring in the Pipelines." International Journal of Pressure Vessels and Piping, vol. 111-112, pp. 99-105, Nov. 1, 2013.

\* cited by examiner

APPARATUS AND METHOD FOR MEASURING FLOWABLE SUBSTANCE AND ARRANGEMENT AND METHOD FOR CONTROLLING SOLID CONTENT OF FLOWABLE SUBSTANCE

FIELD

The invention relates to an apparatus and a method for measuring flowable substance and an arrangement and a method for controlling solid content of the flowable substance.

BACKGROUND

One of the biggest problems in measurement of sewage sludge or any other flowable substance is a dirt build-up on the sensor elements which are in contact with the flowable substance. The effect of the layered dirt on the microwave sensor elements may cause an error of up to tens of percentages to a measurement result. Such a huge error may lead to wrong control of a process, excessive or imbalanced use of chemical agents or other input material and also economic losses. Thus, there is a need for improvement in the microwave measurement of flowable substance.

BRIEF DESCRIPTION

An object of the present invention is to provide improvement to the prior art. The objects of the invention are achieved by apparatus of the independent claim 1.

According to another aspect of the present invention, there is provided an independent control arrangement claim 7.

According to another aspect of the present invention, there is provided an independent measurement method claim 10.

According to another aspect of the present invention, there is provided an independent control method claim 11.

The preferred embodiments of the invention are disclosed in the dependent claims.

The invention provides advantages. The effect of dirt layers on the sensor elements in contact with the flowable substance can be reduced or eliminated.

LIST OF THE DRAWINGS

In the following the invention will be described in greater detail by means of preferred embodiments with reference to the attached drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments, they are simplified diagrams that only show some structures and/or functional entities. The connections shown in these Figures may refer to logical or physical connections. Interfaces between the various elements may be implemented with suitable interface technologies. It is apparent to a person skilled in the art that the described apparatuses may also comprise other functions and structures. Therefore, they need not be discussed in more detail here. Although separate single entities have been depicted, different parts may be implemented in one or more physical or logical entities.

Figure 1:
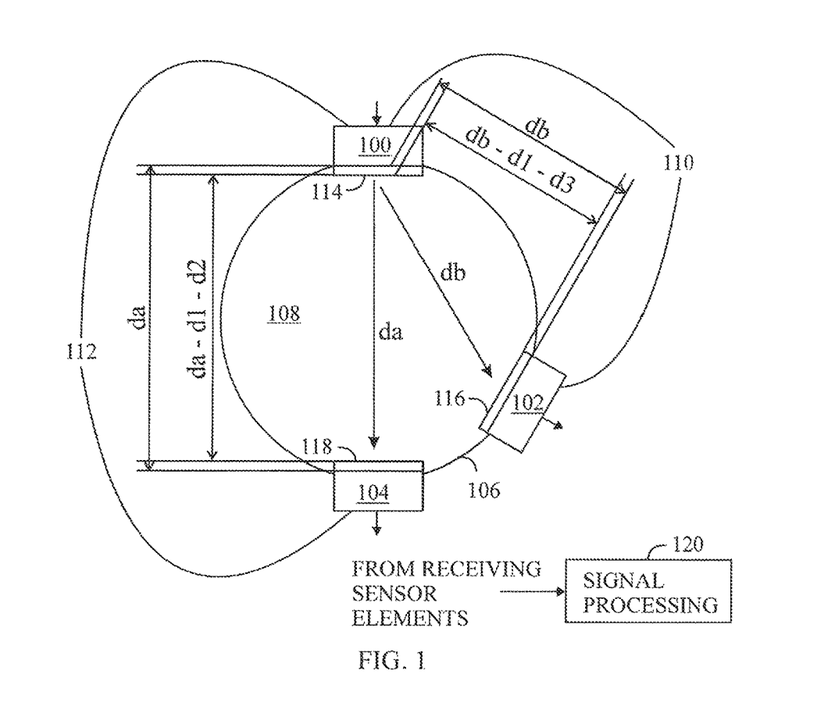
FIG. 1 illustrates an example of a first measurement configuration.

FIG. 1 shows an example of an apparatus for measuring flowable substance. The apparatus comprises at least three microwave sensor elements 100, 102, 104 which are arranged at separate locations in a measurement chamber 106 in contact with the flowable substance 108. The substance 108 may be stationary in the chamber 106 during measurement or the substance may flow through the chamber 106 (i.e. a flow-through chamber or a process pipe). The flowable substance 108 may be suspension such as sewage sludge or pulp, for example.

The flowable substance 108 builds up dirt layers 114, 116, 118 of solid material on the microwave sensor elements 100 to 104. The dirt layers of sewage sludge may comprise various kinds of solid material, for example polymer. In pulp the dirt layers may be made of any solid material mixed in the pulp such as fibers, fillers, retention agents, resin, colouring agent, for example. The dirt layers have a different relative dielectric constant from that of water which is the dominating medium in pulp slurry and sewage sludge. The unknown thickness of dirt layer 114, 116, 118 with known or unknown dielectric constant deteriorates the accuracy of a measurement based on a time of flight of a microwave signal between sensor elements. The time of flight may be measured by determining a phase of the microwave signal, by measuring the actual flight time or any other method to determine microwave signal delay.

The sensor elements 100 to 104 operate as at least two transmitter-receiver pairs 110, 112. In the example of FIG. 1, a transmitting sensor element 100 transmits microwave signals via at least two paths da, db through dirt layers 114, 116, 118 and the flowable substance 108 to at least two receiving sensor elements 102, 104. The path variables da and db refer to a length of the paths.

Figure 2:
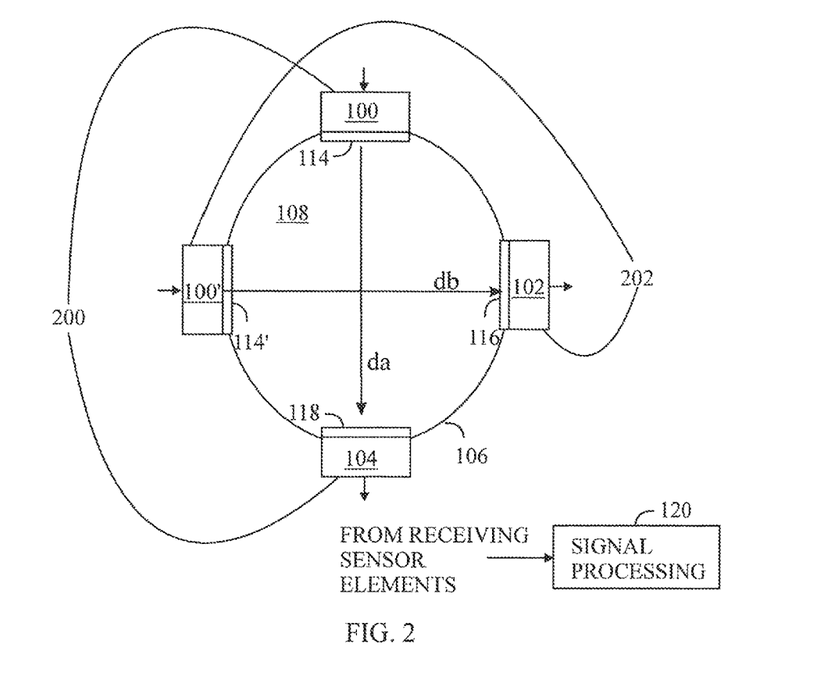
FIG. 2 illustrates an example of a second measurement configuration.

FIG. 2 illustrates an example where a transmitting sensor element 100 transmits a microwave signal via a path da through dirt layers 114, 118 the flowable substance 108 to a receiving sensor element 104, and another transmitting sensor element 100' transmits a microwave signal via a path db through dirt layers 114', 116 and the flowable substance 108 to the sensor element 102. In FIG. 2, a first transmitter-receiver pair 200 is formed with the transmitting element 100 and the receiving element 104. The second transmitter-receiver pair 202 is formed with the transmitting element 100' and the receiving element 102.

Figure 3:
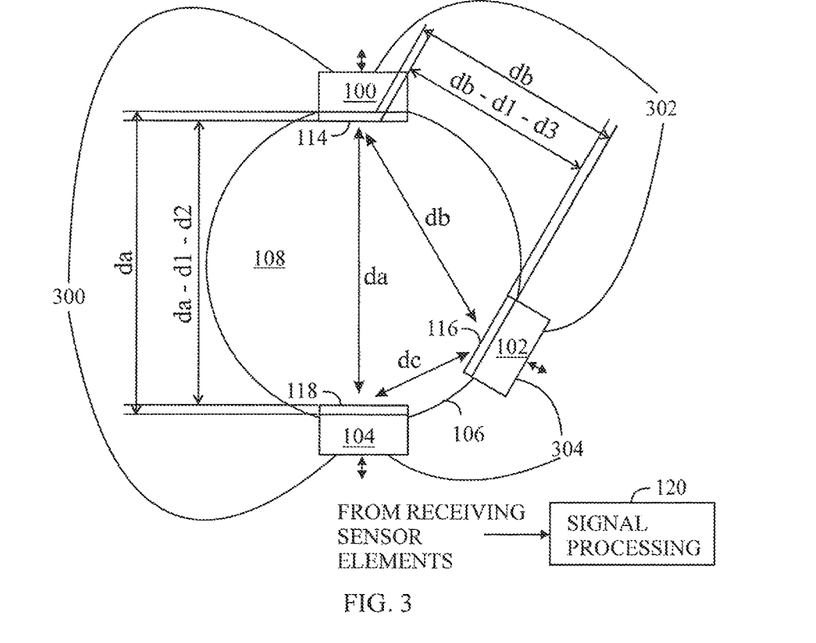
FIG. 3 illustrates an example of a third measurement configuration.

FIG. 3 illustrates an example where a transmitting sensor element 100 transmits microwave signals via paths da, db through the dirt layers 114, 116, 118 and the flowable substance 108 to receiving sensor elements 102, 104. The receiving sensor element 104 may in this example be a transceiving sensor element and the sensor element 104 may transmit a microwave signal via a path dc through dirt layers 116, 118 and the flowable substance 108 to the sensor element 102. The path variable dc refers to a length of the path. In FIG. 3, a first transmitter-receiver pair 300 is formed with the transmitting element 100 and the receiving element 104. The second transmitter-receiver pair 302 is formed with the transmitter sensor element 100 and the receiving element 102. The third transmitter-receiver pair 304 is formed with the transmitting element 104 and the receiving element 102.

Figure 4:
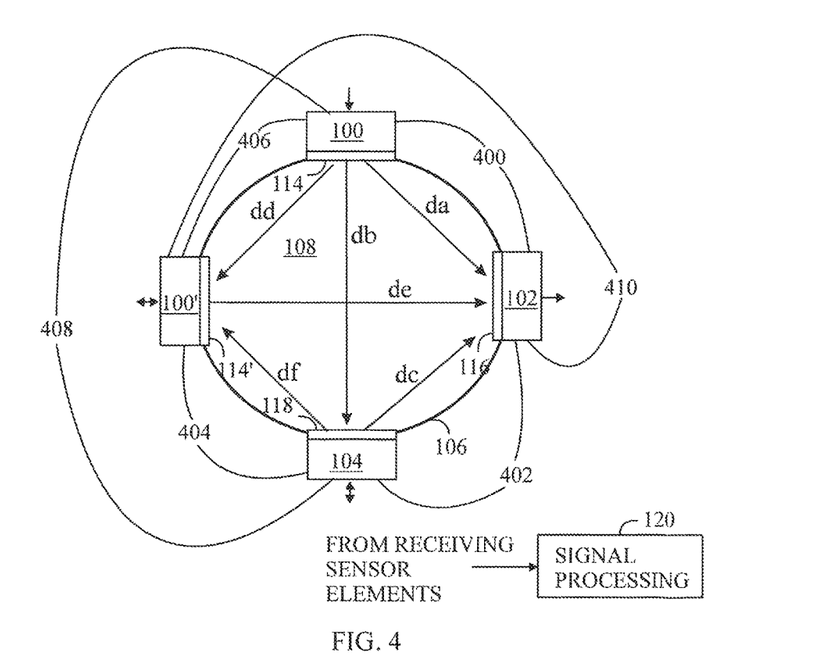
FIG. 4 illustrates an example of a fourth measurement configuration.

FIG. 4 illustrates an example where a transmitting sensor element 100 transmits microwave signals via paths da, db, dd through dirt layers 114, 114', 116, 118 and the flowable substance 108 to receiving sensor elements 100', 102, 104. The path variable dd refers to a length of the path. The transmitting sensor element 100' which is a transceiver element, transmits a microwave signal via path de through dirt layers 114', 116 and the flowable substance 108 to the sensor elements 102. The path variable de refers to a length of the path. The transmitting sensor element 104 which is a transceiver element, transmits a microwave signal via path df through dirt layers 114', 118 and the flowable substance 108 to the sensor elements 100'. The path variable df refers to a length of the path. The transmitting sensor element 104 may also transmit a microwave signal via path dc through dirt layers 116, 118 and the flowable substance 108 to the sensor elements 102. In FIG. 4, a first transmitter-receiver pair 400 is formed with the transmitting element 100 and the receiving element 102. A second transmitter-receiver pair 402 is formed with the transmitting element 104 and the receiving element 102. A third transmitter-receiver pair 404 is formed with the transmitting element 104 and the receiving element 100'. A fourth transmitter-receiver pair 406 is formed with the transmitting element 100' and the receiving element 100'. A fifth transmitter-receiver pair 408 is formed with the transmitting element 100 and the receiving element 104. A sixth transmitter-receiver pair 410 is formed with the transmitting element 100' and the receiving element 102.

The measurement configuration examples of which are shown in FIGS. 1 to 4 can be used to eliminate an effect of dirt layers 114, 114', 116, 118 on the sensor elements 100 to 104 from a measurement result.

Analyse now the example of FIG. 1. The effective distance deff1 between the sensor element 100 and the sensor element 102 may be expressed as:

$$deff1=(db-d1-d3)*\sqrt{\varepsilon_m}+d1*\sqrt{\varepsilon_d}+d3*\sqrt{\varepsilon_d},$$

where d1 and d3 are the thicknesses of the dirt layers on the sensor elements 100 and 102, $\varepsilon_m$ is the relative dielectric constant of the flowable substance 108, which is typically water dominant liquid-like flowing substance, and $\varepsilon_d$ the relative dielectric constant of the dirt layers. The effective distance means the distance of the microwave signal travelling with the speed of light in vacuum in the measured time of flight.

The effective distance deff2 between the sensor element 100 and the sensor element 104 may be expressed as:

$$deff2=(da-d1-d2)*\sqrt{\varepsilon_m}+d1*\sqrt{\varepsilon_d}+d2*\sqrt{\varepsilon_d}.$$

where d2 is the thickness of the dirt layer on the sensor element 104. The difference of effective distances of deff1 and deff2 may be expressed as:

$$\Delta deff=(da-db+d3-d2)*\sqrt{\varepsilon_m}+(d2-d3)*\sqrt{\varepsilon_d}.$$

If the dirt layer d2 118 has the same thickness as the dirt layer d3 116, the difference of effective distances may be expressed as:

$$\Delta deff=(da-db)*\sqrt{\varepsilon_m},$$

which has no dependence from the dirt layers. The mathematics for FIG. 3 is similar.

Analyse now the example of FIG. 2. The effective distance deff1 between the sensor element 100 and the sensor element 104 may be expressed as:

$$deff1=(da-d1-d2)*\sqrt{\varepsilon_m}+d1*\sqrt{\varepsilon_d}+d2*\sqrt{\varepsilon_d},$$

where $\varepsilon_m$ is the relative dielectric constant of layer, which is typically water dominant liquid-like flowing substance, for example, and $\varepsilon_d$ the relative dielectric constant of the dirt layers.

The effective distance means the distance of the microwave signal travelling with the speed of light in vacuum in the measured time of flight. That is, the value of the relative dielectric constant makes the effective distance longer than the actual distance because it takes more time to propagate a distance in material than to travel the same distance in vacuum. The effective distance corresponds to a product of the actual distance and a square root of the relative dielectric constant. The time of flight of a microwave signal may be determined to be the effective distance divided by the speed of light in vacuum. The time of flight depends on a consistency or solid content of the flowable substance, for example.

The effective distance deff2 between the sensor element 100' and the sensor element 102 may be expressed as:

$$deff2=(db-d4-d3)*\sqrt{\varepsilon_m}+d4*\sqrt{\varepsilon_d}+d3*\sqrt{\varepsilon_d}.$$

where d4 is the thickness of the dirt layer 114' on the sensor element 100'.

The difference of effective distances of deff1 and deff2 may be expressed as:

$$\Delta deff=(da-db)*\sqrt{\varepsilon_m}+(d3-d1)*\sqrt{\varepsilon_m}+(d3-d2)*\sqrt{\varepsilon_m}+(d4-d1)*\sqrt{\varepsilon_m}+(d4-d2)*\sqrt{\varepsilon_m}+[(d1-d3)*\sqrt{\varepsilon_d}+(d1-d4)*\sqrt{\varepsilon_d}+(d2-d3)*\sqrt{\varepsilon_d}+(d2-d4)*\sqrt{\varepsilon_d}].$$

If all dirt layers have the same thickness and the same relative dielectric constant, the difference of effective distances becomes $\Delta deff=(da-db)*\sqrt{\varepsilon_m}$, which independent from the dirt layers. In this example, the distance da is different from the distance db, i.e. the distance da is not the same as distance db, da≠db.

Analyse now the example of FIG. 4. The effective distance deff1 between the sensor element 100 and the sensor element 102 may be expressed as:

$$deff1=(da-d1-d3)*\sqrt{\varepsilon_m}+d1*\sqrt{\varepsilon_d}+d3*\sqrt{\varepsilon_d},$$

where $\varepsilon_m$ is the relative dielectric constant of layer, which is typically water dominant liquid-like flowing substance, and $\varepsilon_d$ the relative dielectric constant of the dirt layers. The effective distance means the distance of the microwave signal travelling with the speed of light in vacuum in the measured time of flight.

The effective distance deff2 between the sensor element 100 and the sensor element 104 may be expressed as:

$$deff2=(db-d1-d2)*\sqrt{\varepsilon_m}+d1*\sqrt{\varepsilon_d}+d2*\sqrt{\varepsilon_d}.$$

The effective distance deff3 between the sensor element 100 and the sensor element 100' may be expressed as:

$$deff3=(dd-d1-d4)*\sqrt{\varepsilon_m}+d1*\sqrt{\varepsilon_d}+d4*\sqrt{\varepsilon_d}.$$

The effective distance deff4 between the sensor element 100' and the sensor element 102 may be expressed as:

$$deff4=(de-d3-d4)*\sqrt{\varepsilon_m}+d3*\sqrt{\varepsilon_d}+d4*\sqrt{\varepsilon_d}.$$

The effective distance deff5 between the sensor element 104 and the sensor element 102 may be expressed as:

$$deff5=(dc-d2-d3)*\sqrt{\varepsilon_m}+d2*\sqrt{\varepsilon_d}+d3*\sqrt{\varepsilon_d}.$$

The effective distance deff6 between the sensor element 104 and the sensor element 100' may be expressed as:

$$deff6=(df-d2-d4)*\sqrt{\varepsilon_m}+d2*\sqrt{\varepsilon_d}+d4*\sqrt{\varepsilon_d}.$$

Now all dirt layers d1, d2, d3 and d4 (114, 114', 116, 118) can be cancelled out without any assumption of their thickness, and the difference of effective distances Δdeff becomes Δdeff=(da−db)*$\sqrt{\varepsilon_m}$, which independent from the dirt layers. Actually, the difference of effective distances Δdeff may be formed between any transmitter-receiver pair, i.e. over any distances da, db, dc, de and df. Mathematically this may be expressed as Δdeff=(dx−dy)*$\sqrt{\varepsilon_m}$, where x may be a, b, c, e or f, y may be a, b, c, e or f, and x may not be the same as y.

The effective distance deff corresponds to the time of flight. The longer the time of flight, the longer the effective distance and vice versa. In a similar manner, the longer the time of flight, the larger the phase-shift of the microwave signal. The difference of the effective distance behaves in a corresponding manner, because the measurement is a function of the relative dielectric constant $\varepsilon_m$ of the flowable substance 108 in the chamber 106.

In an embodiment, the apparatus may comprise a signal processing unit 120 which receives signals from the at least two transmitter-receiver pairs 110, 112. The signals may be the same as received by the receiving sensor elements or signals pre-processed in the receiving sensor elements. Each signal carries information about a time of flight through a path. The signal processing unit 120 then forms a value of a desired property of the flowable substance 108 on the basis of the pieces of information about the time of flights. The value v of the desired property may be a function of the difference of effective distances Δdeff as follows: v=f(Δdeff). Several measurement results may be combined by averaging.

In an embodiment, the signal processing unit 120 may form the value of the desired property of the flowable substance on the basis of differences between the pieces of information about the time of flights received from the at least two transmitter-receiver pairs.

In an embodiment, at least one transmitting sensor element may transmit a microwave signal to at least two receiving sensor elements which are physically separate from the at least one transmitting sensor element. The angle of transmission may be wide such as 90°, for example. In this manner, the same microwave signal may be received by at least two receiving sensor elements.

In an embodiment, the apparatus may comprises N microwave sensor elements 100, 100', 102, 104 which operate as N separate transmitter-receiver pairs 110, 112, 200, 202, 300, 302, 304, 400, 402, 404, 406, 408, 410, where N is at least two.

In an embodiment, at least two different pairs may have physically separate receiving sensors. In this case, the same transmitting sensor element may transmit to at least two separate receiving sensor elements, for example. Pairs 110, 112 in FIG. 1 are an example of this. At least two different pairs may have physically separate transmitting sensors. Examples of this configuration are pairs 400, 402 in FIG. 4. At least two different pairs may have both a physically separate receiving sensor and a physically separate transmitting sensor. Example of this configuration is pairs 200, 202 in FIG. 2.

In an embodiment, a measuring chamber 106, which may have at least almost a circular circumference, a transmitting element of a transmitter-receiver pair may transmit in a direction of a chord towards a receiving element which is the transmitting element's pair.

In an embodiment, a measuring chamber 106, which may have a at least almost circular circumference, a transmitting element of a transmitter-receiver pair may transmit in a direction of a diameter towards a receiving element which is the transmitting element's pair.

Figure 5:
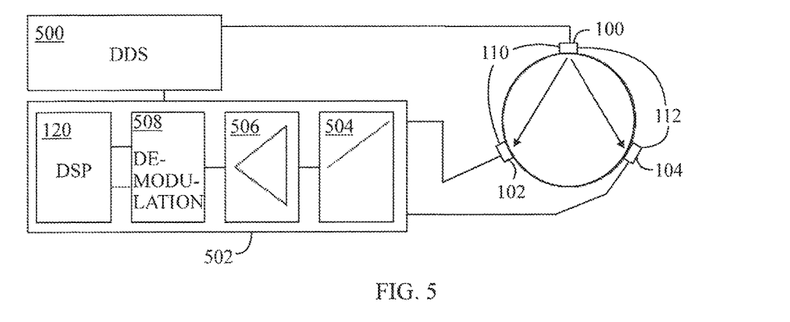
FIG. 5 illustrates an example of a first measurement arrangement.

FIG. 5 illustrates an example of the apparatus a little bit more. A DDS (Direct-Digital-Synthesizer) may be a source 500 of the microwave radiation which is fed to a transmitting element 100. The source of microwave radiation may also be analog based on phase-lock-loop, for example. A digital source is stable and doesn't need a drift correction which on the other hand is necessary for an analog source. In a digital arrangement, both the transmitter and the receiver may be digital the operation of which is based on a single crystal. The transmitting element 100 transmits the microwave signal to receiving elements 102 and 104. The receiver unit 502 may have a switch 504 for alternatively selecting a receiving element 102, 104 from which a received signal may be measured. The receiver unit 502 may also comprise an amplifier 506 for amplifying the selected microwave signal. Additionally, the receiver unit 502 may comprise a demodulator 508 by which the amplitude and phase of the signal can be determined. The demodulator 508 may be an IQ-demodulator, for example. After demodulation the signal may be converted from an analog signal to a digital signal (not shown in FIG. 5). Finally, the receiver unit 502 may comprise a digital signal processor 120 which performs signal processing and forms a value for the desired property of the flowable substance 108. The desired property may be consistency, density, solid matter content, water content or the like. The signal processor 120 may detect a phase difference between the received signals received from the chamber 106. There is no need for a reference signal to be fed to the signal processor 120 from the source 500 passed through a constant reference path.

The transmitting element 100 and the receiving element 102 may be directed to each other at least approximately in a similar manner as the transmitting element 100 and the receiving element 104. That is, their deviation from a direction, which is normal to the surface of the transmitting element 100, has the same absolute value (the magnitude of the deviation may be the same but the angles may have opposite signs). In this manner, the length through both the dirt layer on the transmission element 100 and the dirt layer on the receiving element 102 is the same as the length through both the dirt layer on the transmitting element 100 and the dirt layer on the receiving element 104. The effect could be achieved by tilting the transmitting and receiving elements 100, 102, 104 in such positions irrespective of their location in the measurement chamber 106.

Figure 6:
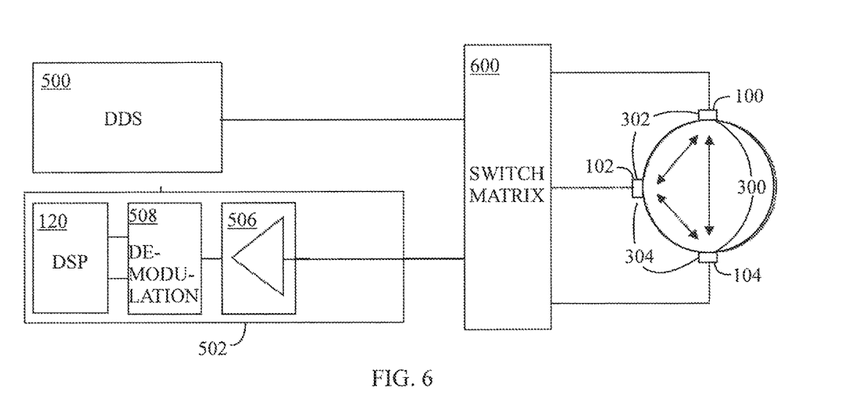
FIG. 6 illustrates an example of a second measurement arrangement.

FIG. 6 illustrates another example of the apparatus which has a switch matrix 600 which may temporarily couple any one of the sensor elements 100, 102, 104 and the source 500 together for transmitting the microwave radiation through the flowable substance 108. The switch matrix 600 may also temporarily couple any of the sensor elements 100, 102, 104, which is different from that coupled with the source 500 at that moment, with the receiver unit 502. In this manner, any combination of sensor elements 100, 102, 104 and all paths through the flowable substance 108 may be utilized in the measurement. By using switch matrix 600 it is possible to have an improved result from the measurement.

Figure 7A:
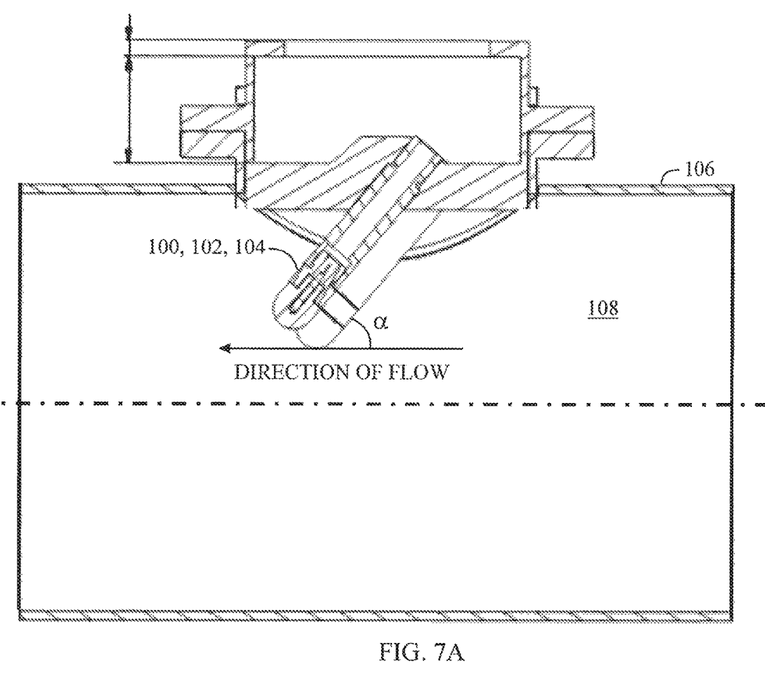
FIG. 7A illustrates an example of structure of sensor elements.
Figure 7B:
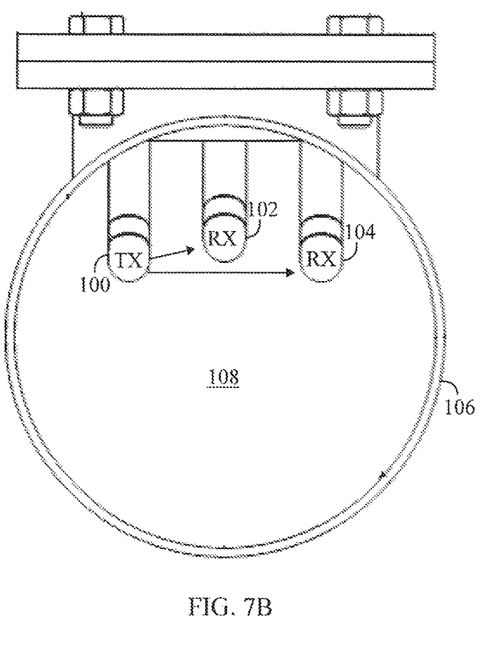
FIG. 7B illustrates a side view of the sensor elements of FIG. 7A.

FIGS. 7A and 7B illustrate finger-like elongated sensor elements 100, 102, 104 in a flow-through chamber 106 which may be a tube. The finger-like sensor element 100 to 104 may be tilted such that their longitudinal axis has an angle α with respect to the direction of flow of the flowable substance 108 which is less than 90° measured between the finger-like sensor element and the flow approaching the finger-like sensor element. The sensor element heads in the flowable substance 108 may be made of ceramic material. The sensor elements 100, 102, 104 may be monopoles.

In an embodiment, the distance in the direction of transmission of the microwave radiation between the sensor elements 100, 102, 104 is shorter than a double distance between any of the sensor elements 100, 102, 104 and the wall of the chamber 106. This kind of configuration reduces the effects of reflection from the walls of the chamber 106. Note that the microwave radiation is mainly transmitted in direction where the wall reflection is in the direction away from the sensor in FIG. 7A. That is why there is practically no disturbing reflections from the wall above the sensor elements 100, 102, 104 although the distance between the wall above and the sensor elements 100, 102, 104 is rather short.

Figure 8A:
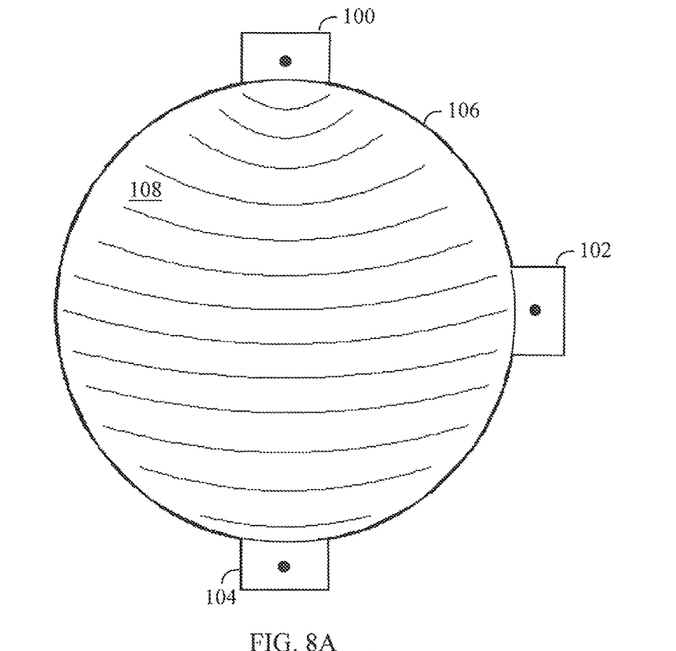
FIG. 8A illustrates an example of polarizing the electric field parallel with the walls of the measurement chamber.
Figure 8B:
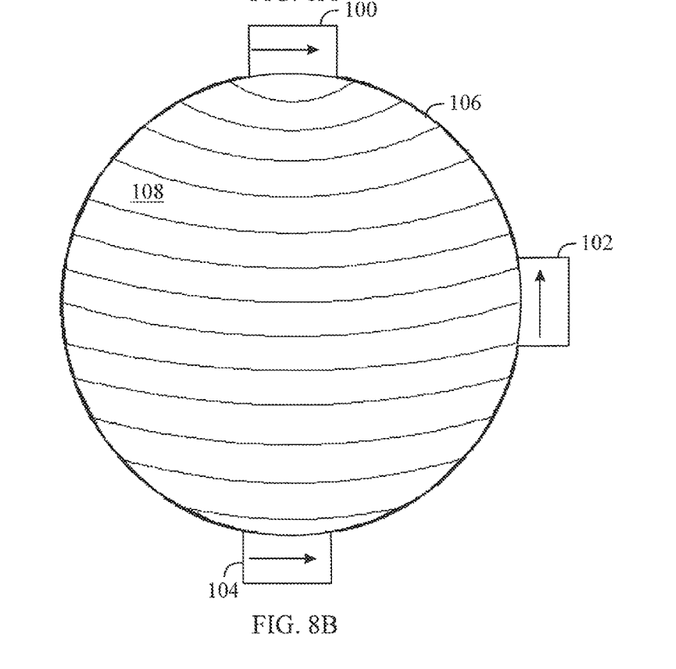
FIG. 8B illustrates an example of polarizing the electric field perpendicular to the walls of the measurement chamber.

FIGS. 8A and 8B show possible directions of electric field. If the electric field is polarized parallel (marked as dot in FIG. 8A) to the wall direction of the chamber 106 and if the chamber 106 comprises electrically conducting material such as metal as shown in FIG. 8A, the electric field is zero on the chamber wall. The wall direction is perpendicular to a normal of the wall surface, and the wall direction is also a direction parallel to the longitudinal axis of a tube-like chamber. In this way, the potential dirt layer on the wall of the chamber 106 doesn't disturb the measurement with the microwave radiation.

If the electric field is polarized perpendicular to the walls of the chamber 106, the electric field is not zero on the electrically conduction walls of the chamber 106. In this case, the dirt layer on the walls of chamber 106 has an effect on the measurement performed with the microwave radiation. The frequency of the microwave radiation may be in the range of 1 GHz to 5 GHz. In an embodiment, the frequency is one of the following: 2 GHz, 3 GHz or 4 GHz within an inaccuracy of 1 GHz. In any case, the frequency of the microwave radiation may be selected to be as high as possible to avoid or to reduce the effects of conductance.

Figure 9:
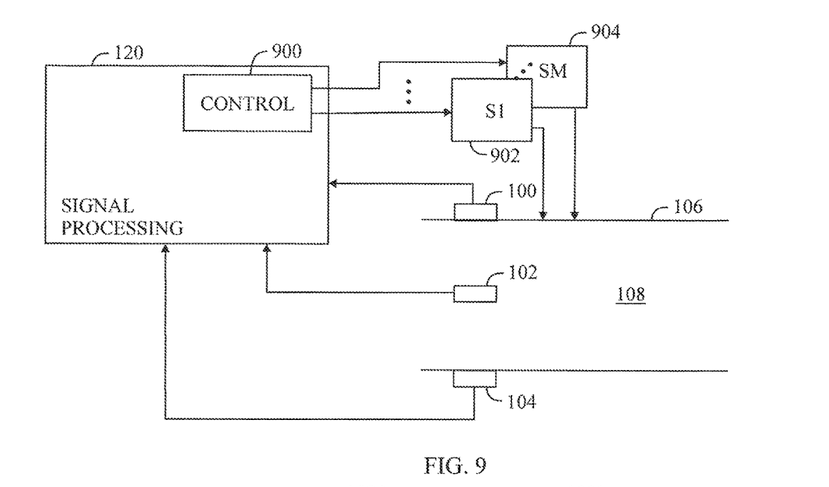
FIG. 9 illustrates an example of a control arrangement.

FIG. 9 presents an example of a control arrangement for controlling solid content of flowable substance 108. The control arrangement comprises at least three microwave sensor elements 100, 102, 104 which are arranged at separate locations in a measurement chamber 106 in contact with the flowable substance 108. The sensor elements 100, 102, 104 operate as at least two transmitter-receiver pairs 110, 112. Each pair 110, 112 transmits a microwave signal via a unique path through the flowable substance 108 for eliminating an effect of dirt layer 114, 116, 118 on the sensor elements 100, 102, 104 from the measurement result. The control arrangement comprises a signal processing unit 120 configured to receive signals from the at least two transmitter-receiver pairs 110, 112 and form a value of a desired property of the flowable substance 108 on the basis of the signals from the at least two transmitter-receiver pairs 110, 112. The signal processing unit 120 also comprises a controller 900 which controls feed of at least one substance S1 to SM, where M is one or a larger integer, which has an effect on the measured value of the flowable substance 108 to the chamber 106 on the basis of the value of the desired property of the flowable substance 108. The control may be based on ratio control.

In an embodiment, the controller 900 controls feed of at least one chemical which causes and/or activates sedimentation in the flowable substance. In this example, the flowable substance may be sewage sludge. Each chemical may come from a container 902 to 904 the output of which to the chamber 106 and into the flowable substance 108 is controlled by the controller 900. In an embodiment, an increase of the feed of the at least one chemical to the flowable substance 108 by the controller 900 may be proportional to a measured property of the flowable substance 108. That is, if the solid content is high in the flowable substance 108, the higher the amount of the at least one chemical which is fed to the flowable substance 108 and vice versa.

At least one chemically enhanced primary treatment (CEPT) agent may be added to the sewage sludge in a controlled manner. A CEPT agent may comprise metal salts and/or polymers. The CEPT agent causes the suspended particles in the flowable substance 108 to aggregate together and form flocs or clots which makes the water treatment easier and faster in a water treatment plant.

In an embodiment, the controller 900 controls the feed of solid particles which have a different relative dielectric constant than the medium of the flowable substance 108 to the chamber 106. For example the percentage of fibers or other solid particles may be increased or decreased in suspension of pulp in this manner.

In an embodiment, the controller 900 controls the amount of the at least one substance fed to the chamber in a batch process. In an embodiment, the controller 900 controls the amount of the at least one substance fed to the chamber in a time unit in a continuous process.

Figure 10:
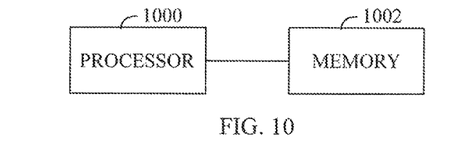
FIG. 10 illustrates an example of a processor and memory.

In an embodiment shown in FIG. 10, the signal processing unit 120 may comprise at least one processor 1000 and at least one memory 1002 including a computer program code. A computer program product may be embodied on a distribution medium readable by a computer and may comprise the program code which, when loaded into the at least one memory 1002 of the signal processing unit 120, causes the signal processing unit 120 to perform at least one of the step required by the measurement or the control.

The at least one computer program may be placed on a computer program distribution means for the distribution thereof. The computer program distribution means is readable by at least one data processing device for encoding the computer program commands and carrying out the actions.

The distribution medium, in turn, may be a medium readable by a data processing device, a program storage medium, a memory readable by a data processing device, a software distribution package readable by a data processing device, a signal readable by a data processing device, or a compressed software package readable by a data processing device. In some cases the distribution medium may also include a telecommunication signal readable by a data processing device.

Figure 11:
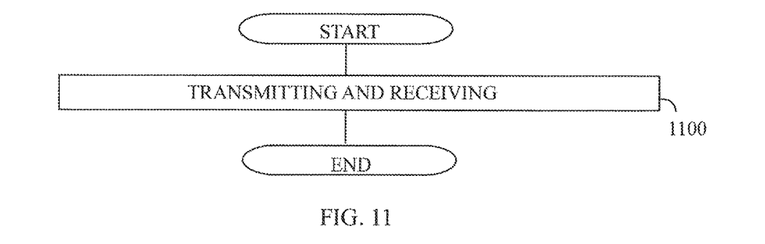
FIG. 11 illustrates an example of a flow chart of a measurement method.

FIG. 11 presents an example of a measurement method. In step 1100, microwave radiation is transmitted and received with at least two transmitter-receiver pairs 110, 112, 200, 202, 300, 302, 304, 400, 402, 404, 406, 408, 410 via at last different two paths through the flowable substance 108, the transmitter-receiver pairs 110, 112, 200, 202, 300, 302, 304, 400, 402, 404, 406, 408, 410 being formed with at least three microwave sensor elements 100, 100', 102, 104 arranged at separate locations in a measurement chamber 106 in contact with the flowable substance 108 for eliminating an effect of dirt layers 114, 114', 116, 118 on the sensor elements 100, 100', 102, 104 from the measurement result.

Figure 12:
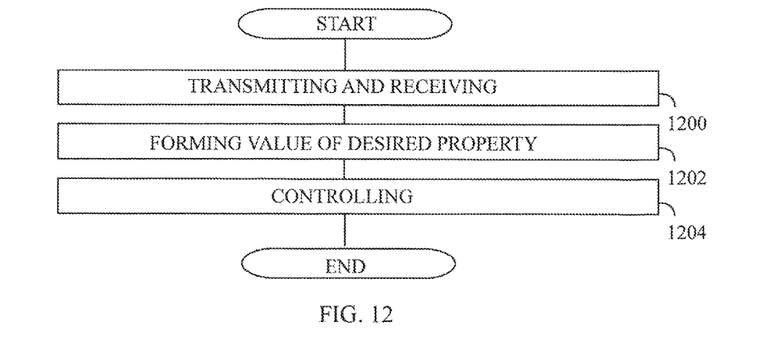
FIG. 12 illustrates an example of a flow chart of a control method.

FIG. 12 presents an example of a control method. In step 1200, microwave radiation is transmitted and received with at least two transmitter-receiver pairs 110, 112, 200, 202, 300, 302, 304, 400, 402, 404, 406, 408, 410 via at last different two paths through the flowable substance 108, the transmitter-receiver pairs 110, 112, 200, 202, 300, 302, 304, 400, 402, 404, 406, 408, 410 being formed with at least three microwave sensor elements 100, 100', 102, 104 arranged at separate locations in a measurement chamber 106 in contact with the flowable substance 108 for eliminating an effect of dirt layers 114, 114', 116, 118 on the sensor elements 100, 100', 102, 104 from the measurement result. In step 1202, a value of a desired property of the flowable substance 108 is formed on the basis of pieces of information carried by the received microwave radiation. In step 1204, the feed of the at least one substance which has an effect on the measured value of the flowable substance 108 to the chamber 106 is controlled on the basis of the measured value of the desired property of the flowable substance 108.

All in all, the solution may be implemented as one or more integrated circuits, such as application-specific integrated circuits ASIC (Application Specific Integrated Circuit). Other hardware embodiments are also feasible, such as a circuit built of separate logic components. A hybrid of these different implementations is also feasible. When selecting the method of implementation, a person skilled in the art will consider the requirements set for the size and power consumption of the apparatus, the necessary processing capacity, production costs, and production volumes, for example.

The solution with many embodiments presented in this document may be applied in a water treatment plant, a paper mill, production of pulp, pharmaceutical industry or the like. The solution described in this application reduces or eliminates an error in a measurement result caused by the dirt layer on the sensor elements. This provides a more accurate result of the measured property which may be used in the process control. The error in a consistency measurement because of the dirt build-up may be particularly high in low consistencies, for example, but the error exists also in high consistencies. The error may be as high as 50%, for example.

It will be obvious to a person skilled in the art that, as the technology advances, the inventive concept can be implemented in various ways. The invention and its embodiments are not limited to the examples described above but may vary within the scope of the claims.

The invention claimed is:

1. An apparatus for measuring a flowable substance which comprises:
    at least three microwave sensor elements arranged at separate locations in a measurement chamber in contact with the flowable substance, wherein the at least three microwave sensor elements comprise only an odd number of sensor elements; and
    said sensor elements being configured to operate as at least two transmitter-receiver pairs, distances between any two transmitter-receiver sensor element pairs deviating from each other, the at least two transmitter-receiver sensor element pairs being configured to transmit and receive microwave radiation via at least two paths of different lengths, through layers of dirt on the sensor elements and the flowable substance;
    a switch matrix configured to temporarily form couplings between the sensor elements;
    a source and a receiver for transmitting the microwave radiation through the flowable substance using different combinations of the sensor elements temporarily coupled by the switch matrix; and
    a signal processing unit configured to receive signals via the at least two paths of different lengths between the at least two transmitter-receiver sensor element pairs, the signals carrying pieces of information about time of flights between the at least two transmitter-receiver pairs, and form a value of a desired property of the flowable substance on the basis of the pieces of information about the time of flights, and eliminate an effect of dirt layers on the sensor elements from the value of the desired property.

2. The apparatus as claimed in claim 1, wherein the signal processing unit is configured to form the value of the desired property of the flowable substance on the basis of differences in pieces of information about the time of flights.

3. The apparatus as claimed in claim 1, wherein at least one transmitting sensor element is configured to transmit a microwave signal to at least two receiving sensor elements.

4. The apparatus as claimed in claim 1, wherein the apparatus comprises N microwave sensor elements configured to operate as N separate transmitter-receiver pairs, where N is at least two and different pairs have a physically separate receiving sensor, a physically separate transmitting sensor or both a physically separate receiving sensor and a physically separate transmitting sensor.

5. The apparatus as claimed in claim 1, wherein in a measuring chamber, which has a circular circumference, a transmitter of the at least two transmitter-receiver sensor element pairs transmits in a direction of a chord towards a corresponding receiver.

6. The apparatus as claimed in claim 1, wherein the chamber comprises electrically conducting material for causing an electric field polarized parallel to the wall direction of the chamber to be zero on the chamber wall.

7. A control arrangement for controlling solid content of a flowable substance, said control arrangement comprising:
    at least three microwave sensor elements arranged at separate locations in a measurement chamber in contact with the flowable substance, wherein the at least three microwave sensor elements comprise only an odd number of sensor elements; said sensor elements being configured to operate as at least two transmitter-receiver sensor element pairs each pair of the transmitter-receiver sensor element pairs being configured to transmit a microwave radiation via a unique length of path through the flowable substance;

a switch matrix configured to temporarily form couplings between the sensor elements;

a source and a receiver for transmitting the microwave radiation through the flowable substance using different combinations of the sensor elements temporarily coupled by the switch matrix; and a signal processing unit configured to receive signals via the unique paths of different lengths carrying information about time of flights from the at least two transmitter-receiver pairs form a value of a desired property of the flowable substance on the basis of the information about the time of flights and eliminate an effect of dirt layers on the sensor elements from the value of the desired property, and the signal processing unit comprises a controller which is configured to control feed of at least one substance which has an effect on the measured value of the flowable substance to the chamber on the basis of the measured value of the desired property of the flowable substance.

8. The arrangement as claimed in claim 7, wherein the controller is configured to control a feed of chemical which causes sedimentation in the flowable substance.

9. The arrangement as claimed in claim 7, wherein the signal processing unit comprises at least one processor; and at least one memory including a computer program code, wherein the at least one memory and the computer program code are configured, with the at least one processor, to cause the signal processing unit at least to perform forming the value of the desired property of the flowable substance on the basis of the information about the time of flights, and controlling the feed of the at least one substance which has an effect on the measured value of the flowable substance to the chamber on the basis of the measured value of the desired property of the flowable substance.

10. A method of measuring flowable substance, the method comprising:

transmitting and receiving with at least two transmitter-receiver pairs microwave radiation via at least two different paths through the flowable substance, the transmitter-receiver pairs being formed with at least three microwave sensor elements arranged at separate locations in a measurement chamber in contact with the flowable substance, the at least three microwave sensor elements comprising only an odd number of sensor elements, distances between any two transmitter-receiver sensor element pairs deviating from each other;

temporarily forming couplings between the sensor elements with a switch matrix;

transmitting the microwave radiation through the flowable substance using a source and a receiver with different combinations of the sensor elements temporarily coupled by the switch matrix; and receiving, by a signal processing unit, signals via the at least two paths of different lengths between the at least two transmitter-receiver pairs, the signals carrying pieces of information about time of flights between the at least two transmitter-receiver pairs, and forming, by the signal processing unit, a value of a desired property of the flowable substance on the basis of the pieces of information about the time of flights and eliminating, by the signal processing unit, an effect of dirt layers on the sensor elements from the value of the desired property.

11. A method for controlling solid content of a flowable substance, the method comprising:

transmitting and receiving with at least two transmitter-receiver sensor element pairs microwave radiation via at least two paths of different lengths through the flowable substance, the transmitter-receiver sensor element pairs being formed with at least three microwave sensor elements arranged at separate locations in a measurement chamber in contact with the flowable substance, the at least three microwave sensor elements comprising only an odd number of sensor elements distances between any two transmitter-receiver sensor element pairs deviating from each other;

temporarily forming couplings between the sensor elements with a switch matrix;

transmitting the microwave radiation through the flowable substance using a source and a receiver with different combinations of the sensor elements temporarily coupled by the switch matrix; and receiving, by a signal processing unit, signals via the at least two paths of different lengths carrying pieces of information about time of flights from the at least two transmitter-receiver sensor element pairs;

forming a value of a desired property of the flowable substance on the basis of pieces of information carried by the received microwave radiation;

eliminating an effect of dirt layers on the sensor elements from the value of the desired property; and controlling the feed of the at least one substance which has an effect on the measured value of the flowable substance to the chamber on the basis of the measured value of the desired property of the flowable substance.

* * * * *